US012629005B2

(12) United States Patent
Chun et al.

(10) Patent No.: US 12,629,005 B2
(45) Date of Patent: May 19, 2026

(54) TUBE MEMBER HAVING EXCELLENT LOCAL BENDABILITY, AND METHOD FOR MANUFACTURING SAME

(71) Applicant: MEDICARETEC CO., LTD., Seoul (KR)

(72) Inventors: Han Yong Chun, Seoul (KR); Kwang Koo Jee, Seoul (KR); Chun Woo Kim, Seoul (KR)

(73) Assignee: MEDICARETEC CO., LTD., Seoul (KR)

( * ) Notice: Subject to any disclaimer, the term of this patent is extended or adjusted under 35 U.S.C. 154(b) by 647 days.

(21) Appl. No.: 18/009,644

(22) PCT Filed: Jun. 4, 2021

(86) PCT No.: PCT/KR2021/007035
§ 371 (c)(1),
(2) Date: Dec. 9, 2022

(87) PCT Pub. No.: WO2021/251695
PCT Pub. Date: Dec. 16, 2021

(65) Prior Publication Data
US 2023/0225786 A1 Jul. 20, 2023

(30) Foreign Application Priority Data

Jun. 9, 2020 (KR) ........................ 10-2020-0069481
Jun. 4, 2021 (KR) ........................ 10-2021-0072460

(51) Int. Cl.
*A61B 1/005* (2006.01)
*A61B 17/00* (2006.01)
(Continued)

(52) U.S. Cl.
CPC .......... *A61B 1/005* (2013.01); *A61B 18/1492* (2013.01); *C22C 19/03* (2013.01);
(Continued)

(58) Field of Classification Search
CPC ........ A61B 18/1492; A61B 2018/0016; A61B 2018/00357; A61B 2018/00613;
(Continued)

(56) References Cited

U.S. PATENT DOCUMENTS 9,775,591 B2 * 10/2017 Delgado ............ A61B 17/0644
2008/0194994 A1 8/2008 Bown et al.
(Continued)

FOREIGN PATENT DOCUMENTS

JP H04-292174 A 10/1992
JP 2003-247053 A 9/2003
(Continued)

*Primary Examiner* — Linda C Dvorak
*Assistant Examiner* — Abigail Bock
(74) *Attorney, Agent, or Firm* — Bridgeway IP Law Group, PLLC; Sang Ho Lee; Hyun Woo Shin

(57) ABSTRACT

The present invention relates to a tube member having excellent local bending properties that is capable of being freely bent only on a given region thereof at a working temperature, thereby enabling the bending angle thereof to be freely adjusted by a user, and a method for manufacturing the tube member. According to the present invention, the tube member having excellent local bending properties, which is made of an alloy, may include a first region and a second region having different alloy structures from each other. According to the present invention, the first region may be in a cold-worked state or have an austenite phase at a given working temperature, and the second region may have a martensite phase at the given working temperature and a yield stress value lower than a yield stress value of the first region.

11 Claims, 6 Drawing Sheets

(51) Int. Cl.

| | |
|---|---|
| *A61B 18/00* | (2006.01) |
| *A61B 18/14* | (2006.01) |
| *C22C 19/03* | (2006.01) |
| *C22F 1/00* | (2006.01) |
| *C22F 1/10* | (2006.01) |

(52) U.S. Cl.
CPC ................ *C22F 1/006* (2013.01); *C22F 1/10* (2013.01); *A61B 2017/00526* (2013.01); *A61B 2018/00327* (2013.01)

(58) Field of Classification Search
CPC .. A61B 2018/00767; A61B 2018/1405; A61B 2018/1467

See application file for complete search history.

(56) References Cited

U.S. PATENT DOCUMENTS

| | | | |
|---|---|---|---|
| 2010/0160724 A1* | 6/2010 | Prisco ................... | A61B 1/009 600/101 |
| 2014/0257203 A1* | 9/2014 | Favier ................ | A61B 17/3403 72/364 |
| 2016/0199097 A1* | 7/2016 | Linderman ........ | A61B 17/8811 606/93 |
| 2017/0119363 A1* | 5/2017 | Nguyen ........... | A61B 17/00234 |
| 2018/0000499 A1 | 1/2018 | Altman et al. | |

FOREIGN PATENT DOCUMENTS

| | | |
|---|---|---|
| JP | 2007-289394 A | 11/2007 |
| JP | 2010-517683 A | 5/2010 |
| KR | 10-1990-0700647 A | 8/1990 |
| KR | 10-0618932 B1 | 9/2006 |
| KR | 10-2015-0049767 A | 5/2015 |
| KR | 10-1535520 B1 | 7/2015 |
| KR | 10-2018-0077244 A | 7/2018 |
| WO | 2016-110854 A1 | 7/2016 |

* cited by examiner

TUBE MEMBER HAVING EXCELLENT LOCAL BENDABILITY, AND METHOD FOR MANUFACTURING SAME

TECHNICAL FIELD

The present invention relates to a tube member having excellent local bending properties and a manufacturing method thereof, and more specifically, to a tube member having excellent local bending properties that is capable of being freely bent only on a specific region thereof at a working temperature, thereby enabling the bending angle thereof to be freely adjusted by a user, and a method for manufacturing the tube member.

BACKGROUND ART

The nasal cavity is a space above and behind the nose in the middle of the face, and the front of the nasal cavity communicates with the outside through the nostrils, while the back of the nasal cavity communicates with the pharynx through the choanae. The paranasal sinuses are hollow, air-filled spaces located within the bones of the skull and face, and they are centered on the nasal cavity and serve to protect the brain in the bones of the skull from external impacts. They include the maxillary sinuses, the frontal sinuses, the ethmoidal sinuses, and the sphenoidal sinuses.

The paranasal sinuses may be different in position according to their types, and accordingly, if a surgical instrument such as a tube member is inserted into the paranasal sinuses through the nostrils, the approach angles of the tube member may be different according to the types of the paranasal sinuses and the body shape of a patient. For example, the sphenoidal sinuses have approach angle differences in the range from 0 to 30°, the frontal sinuses have approach angle differences in the range from 70 to 90°, and the maxillary sinuses have approach angle differences in the range from 110 to 120°. To correspond to the various approach angles according to the types of paranasal sinuses, stainless tube members bent to several approach angles (for example, 0°, 12°, 40°, 60°, 90°, and) 120° are provided as the surgical instrument for the paranasal sinuses.

DISCLOSURE

Technical Problem

However, the stainless tube members used as the conventional surgical instrument for the paranasal sinuses do not satisfy the requirements of various approach angles according to the patient's body shapes or the types of paranasal sinuses, so that the tube members are not located appropriately in position at a desired target. Further, the conventional tube members are made of stainless steel, and accordingly, if the tube members are arbitrarily bent to provide desired approach angles, the tube members are deformed by the slip of dislocation according to the properties of the stainless steel, so that the deformation is locally collected and irreversibly occurs, thereby failing to maintain the circular sectional shapes of the tube members. In specific, the tube members are blocked on their bent portion, and accordingly, it is impossible that the bending angles of the tube members made of the stainless steel are arbitrarily adjusted.

Accordingly, the present invention has been made in view of the above-mentioned problems occurring in the related art, and it is an object of the present invention to provide a tube member having excellent local bending properties that is capable of allowing only a specific region to be freely bent at a time when a given work is performed by a user, thereby enabling the bending angle thereof to be freely adjusted by the user according to his or her working environments, and a method for manufacturing the tube member. However, the object of the present invention is exemplary, and therefore, the scope of the invention may not be limited by the above-mentioned object of the present invention. Further, the tube member of the present invention may be used as the surgical instrument for the paranasal sinuses, but it may be just exemplary. Therefore, the tube member according to the present invention is applicable to all working sites where it is freely bent according to the user's work purposes.

Technical Solution

To accomplish the above-mentioned objects, according to one aspect of the present invention, there is provided a tube member having excellent local bending properties, which is made of an alloy, the tube member including a first region and a second region having different alloy structures from each other.

According to the present invention, the first region may be in a cold-worked state or have an austenite phase at a given working temperature, and the second region may have a martensite phase at the given working temperature and a yield stress value lower than a yield stress value of the first region.

According to the present invention, when the first region has the austenite phase, the first region may have a first phase transformation temperature and the second region may have a second phase transformation temperature higher than the first phase transformation temperature. In this case, the first phase transformation temperature and the second phase transformation temperature may be temperatures at which phase transformation from the low temperature martensite phase into the high temperature austenite phase occurs.

According to the present invention, the first phase transformation temperature may be lower than the given working temperature, and the second phase transformation temperature may be higher than the given working temperature.

According to the present invention, the first region may have one end portion of the tube member, and the second region may be connected to the first region and have the other end portion of the tube member.

According to the present invention, the tube member may further include a third region that is in the cold-worked state or has the austenite phase at the given working temperature. In this case, the first region may have one end portion of the tube member, the third region may have the other end portion of the tube member, and the second region may have one end connected to the first region and the other end connected to the third region to form the middle portion of the tube member.

According to the present invention, the third region may have a third phase transformation temperature, and the third phase transformation temperature may be lower than the given working temperature.

According to the present invention, the third phase transformation temperature may be equal to the first phase transformation temperature.

According to the present invention, one end of the third region, which is the other end of the tube member, may be coupled to a cutting member.

According to the present invention, the given working temperature may be in the range from 10 to 50° C.

According to the present invention, the tube member may be used as a surgical instrument for the paranasal sinuses.

According to the present invention, the tube member may be used as a guide tube member for inserting an electric wire.

According to the present invention, the second region may have the shape bent to a given angle.

According to the present invention, the tube member may be made of any one of a nickel-titanium (Ni—Ti) alloy, a copper-zinc (Cu—Zn) alloy, a gold-cadmium (Au—Cd) alloy, and an indium-talium (In—Ti) alloy.

To accomplish the above-mentioned objects, according to another aspect of the present invention, there is provided a surgical instrument for the paranasal sinuses including a tube member made of an alloy.

According to the present invention, the tube member may include: a first region and a third region having austenite phases at a working temperature at which surgery is performed; and a second region having a martensite phase at the working temperature, wherein one end portion of the third region is coupled to a cutting member, and the first region to the third region have phase transformation temperatures at which phase transformation from the low temperature martensite phase into the high temperature austenite phase occurs. In this case, the phase transformation temperature of the second region may be higher than the phase transformation temperatures of the first region and the third region.

To accomplish the above-mentioned objects, according to yet another aspect of the present invention, there is provided a method for manufacturing a tube member having excellent local bending properties.

According to the present invention, the method may include the steps of: preparing an alloy tube member subjected to cold working and divided into a first region and a second region; bending at least a portion of the second region of the tube member to a given angle; and allowing the second region of the tube member to be subjected to a heat treatment so that the second region has a martensite phase.

According to the present invention, the heat treatment may be performed to allow the second region to have phase transformation from the low temperature martensite phase into a high temperature austenite phase, and the temperature at which the phase transformation occurs may be higher than a working temperature as a temperature at which the bending step of the second region is performed.

According to the present invention, the method may include the steps of: preparing an alloy tube member subjected to cold working and divided into a first region, a second region, and a third region; bending at least a portion of the second region of the tube member to a given angle; allowing the entire region of the tube member to be subjected to a first heat treatment to a first temperature so that the tube member has an austenite phase; and allowing the second region of the tube member to be subjected to a second heat treatment so that the second region has a martensite phase.

According to the present invention, the first and second heat treatments may be performed to allow the regions with the heat treatments to have phase transformation from the low temperature martensite phase into the high temperature austenite phase, and the phase transformation temperature of the second region may be higher than the phase transformation temperature of the first region or the third region.

According to the present invention, the method may include the steps of: allowing an alloy to be subjected to cold working to the form of a tube to prepare a straight line-shaped tube member divided into a first region, a second region, and a third region; bending at least a portion of the second region of the tube member to a given angle; allowing the third region of the tube member to be subjected to a first heat treatment so that the third region has an austenite phase; and allowing the second region of the tube member to be subjected to a second heat treatment so that the second region has a martensite phase.

According to the present invention, the first and second heat treatments may be performed to allow the regions with the heat treatments to have phase transformation from the low temperature martensite phase into the high temperature austenite phase, and the temperature at which the phase transformation of the second region occurs may be higher than a working temperature as a temperature at which the bending step of the second region is performed.

According to the present invention, the method may further include the steps of: allowing the third region of the tube member to be cold to a temperature lower than the first phase transformation temperature; expanding one end of the cold third region to couple a cutting member thereto; and raising a temperature of the third region to a temperature higher than the first phase transformation temperature.

According to the present invention, the alloy tube member may be made of any one of a nickel-titanium (Ni—Ti) alloy, a copper-zinc (Cu—Zn) alloy, a gold-cadmium (Au—Cd) alloy, and an indium-talium (In—Ti) alloy.

Advantageous Effects

According to the present invention, the tube member is freely bent only on the specific region thereof, thereby enabling the bending angle thereof to be freely adjusted by the user according to working environments. Therefore, the tube member according to the present invention is applicable to all working sites where it is freely bent if necessary. For example, if it is desired that the tube member is used as the surgical instrument for the paranasal sinuses, the single tube member is easily adjusted at its bending angle according to various approach angles corresponding to the patient's body shape or the types of paranasal sinuses, so that the tube member inserted into the corresponding paranasal sinus is accurately located in position at a target, thereby easily performing the patient's treatment.

As another example, the tube member according to the present invention is used as the guide member for inserting a member such as an electric wire and the like located at a position where a worker's hand does not reach in various working sites.

Of course, the scope of the invention may not be limited by the above-mentioned advantageous effectiveness.

BEST MODE FOR INVENTION

Figures 1, 2:
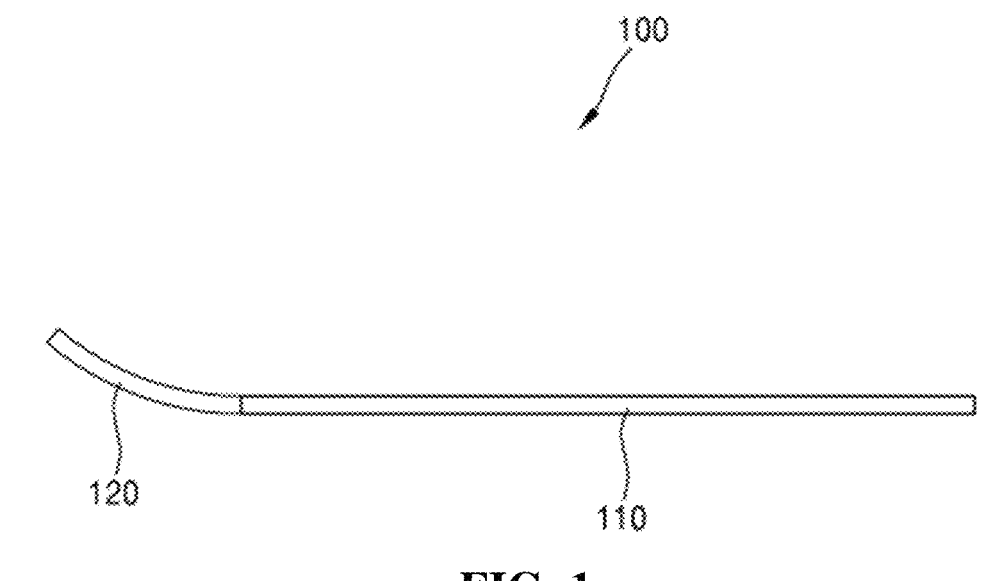
FIG. 1 is a schematic sectional view showing a tube member having excellent local bending properties according to one embodiment of the present invention.
FIG. 2 is a schematic sectional view showing a tube member having excellent local bending properties according to another embodiment of the present invention.

The present invention relates to a tube member having excellent local bending properties that is made of an alloy and includes a first region and a second region having different alloy structures from each other, wherein the first region is in a cold-worked state or has an austenite phase at a given working temperature, and the second region has a martensite phase at the given working temperature and a yield stress value lower than a yield stress value of the first region.

MODE FOR INVENTION

Hereinafter, embodiments of the present invention will be described in detail with reference to the accompanying drawings.

Embodiments of the present invention will be explained in detail so that they may be carried out easily by those having ordinary skill in the art, and before the present invention is disclosed and described, it is to be understood that the disclosed embodiments are merely exemplary of the invention, which can be embodied in various forms. In addition, the example embodiments may be embodied in different forms and should not be construed as limited to the embodiments set forth herein but may be modified and variously implemented by those skilled in the art. Further, the thicknesses or sizes of layers shown in the drawing may be magnified for the clarity and convenience of the description.

Hereinafter, the embodiments of the invention will be described with reference to the accompanying drawings. In the drawings, for example, the shown shapes may be modified according to manufacturing technologies and/or tolerances. Accordingly, the embodiments of the invention are not limited to specific shapes on the regions shown in the description and include, for example, the changes in the shape which is caused by manufacturing.

Figure 3:
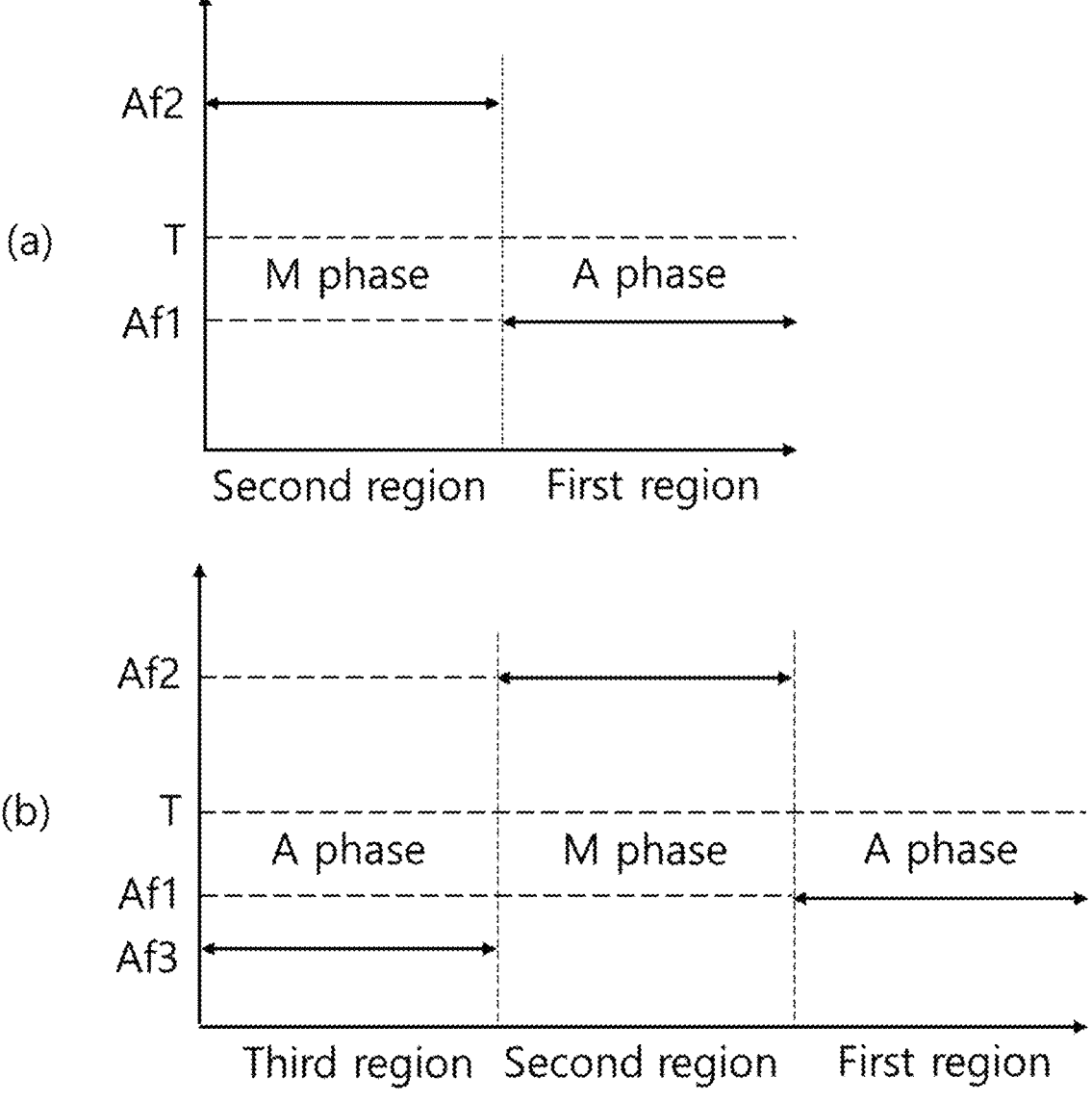
FIG. 3 is a graph showing phase transformation temperatures by region of the tube members of FIGS. 1 and 2.

FIG. 1 is a schematic sectional view showing a tube member 100 according to one embodiment of the present invention, FIG. 2 is a schematic sectional view showing a tube member 200 according to another embodiment of the present invention, and FIGS. 3(a) and 3(b) are graphs showing phase transformation temperatures according to regions 110, 120, and 130 of the tube members 100 and 200 of FIGS. 1 and 2. In this case, the regions of the tube members 100 and 200 are regions forming boundaries, while having different phases from one another on the same tube. Further, the phase transformation temperatures are temperatures at which a low temperature martensite phase transforms into a high temperature austenite phase as a temperature rises.

First, as shown in FIG. 1, the tube member 100 according to one embodiment of the present invention has the shape of a tube made of an alloy and includes the first region 110 and the second region 120. In this case, as shown in FIG. 3(a), the first region 110 and the second region 120 are regions that are different at the phase transformation temperatures Af from the martensite phase (M phase) into the austenite phase (A phase).

In specific, the tube member 100 is made of a nickel and titanium (Ni—Ti) shape memory alloy with 45 to 55 at % Ni, 48 to 55 at % Ni, 45 to 52 at % Ni, or 50 to 51 at % Ni and the balance Ti. In addition to the Ni—Ti alloy, however, the tube member 100 may be made of various types of alloys having the properties of shape memory alloys, such as a copper-zinc (Cu—Zn) alloy, a gold-cadmium (Au—Cd) alloy, an indium-talium (In—Ti) alloy, and the like.

The shape memory alloy has remarkably different crystal arrangements between the parent phase having the high temperature austenite phase and the lower temperature martensite phase, and even after the deformation in shape is applied to the alloy at low temperatures, if the alloy is heated to a temperature higher than a given temperature, it has the shape memory effect so that it recovers to its original phase (the parent phase).

The shape memory effect occurs when the alloy is molded to the shape of the tube by means of cold working and then subjected to a heat treatment at a given temperature, but the tube, which is just subjected to the cold working, has the stress-strain effect, like common alloys.

The tube member 100 includes the straight line-shaped first region 110 easily bent by a user and having given stiffness so that it serves as a support body and the second region 120 freely bendable at a working temperature. In this case, the first region 110 includes one end portion of the tube member 100, and the second region 120 is connected to the first region 100 and has the bent other end portion of the tube member 100.

In this case, the working temperature is a temperature at which the bending of the second region 120 is performed by the user or a temperature in a working environment where the user works with the bent tube member 200.

FIG. 3(a) shows the phases and phase transformation temperatures according to the regions of the tube member 100 as shown in FIG. 1. Referring to FIG. 3(a), the phase transformation temperature Af1 of the first region 110 has a value lower than a working temperature T, and accordingly, the first region 110 has the austenite phase (A phase) at the working temperature T. Contrarily, the phase transformation temperature Af2 of the second region 120 has a value higher than the working temperature T, and accordingly, the second region 120 has the martensite phase (M phase) at the working temperature T.

As a modified example, the second region 120 of the tube member 100 has the martensite phase, and the first region 110 is just cold-worked so that it does not have any characteristics of phase transformation according to the changes in temperature.

The first region 110, which has the austenite phase at the working temperature T or is in a typical cold-worked state, has the given stiffness so that it is grasped by the user or coupled to a separate grip part. Contrarily, the second region 120, which has the martensite phase, has given flexibility so that it is easily deformed even with a small force. An explanation of the second region 120 will be given in detail in another embodiment of the present invention as will be discussed below.

According to another embodiment of the present invention, in the case where the tube member 200 is used as a medical tube member such as a surgical instrument for the paranasal sinuses, it is necessary to mount a cutting member S on the tube member 200 so that the cutting member S enters a human body to remove a surgical site such as an inflamed site. In this case, as shown in FIG. 2, the tube member 200 includes a first region 110 serving as a support body, a second region 120 freely bendable, and a third region 130 for insertedly mounting the cutting member S thereonto. In this case, the cutting member S is made separately from the tube member 200 and coupled to one end of the third region 120, and otherwise, a saw blade-shaped cutting member is formed unitarily at one end of the third region 130.

For example, the first region 110 includes one end portion of the tube member 200, the third region 130 includes the other end of the tube member 200, and the second region 120 has one end connected to the first region 110 and the other end connected to the third region 130 to form the middle portion of the tube member 200. In this case, the second region 120 has the shape bent by a given angle at a given working temperature T, so that the tube member 200 has the shape of a generally bent tube.

The tube member 200 includes the regions having different phase transformation temperatures so that only the specific region can be easily bent at the given working temperature T.

In more specific, as shown in FIG. 3(b), the first region 110 has the austenite phase (A phase) at the given working temperature T and a first phase transformation temperature Af1, and the third region 130 has the austenite phase (A phase) and a third phase transformation temperature Af3. The first phase transformation temperature Af1 of the first region 110 is equal to or different from the third phase transformation temperature Af3 of the third region 130 within the range of temperatures lower than the working temperature T.

Further, the second region 120, which is easily bent by the given angle at the working temperature T, has the martensite phase (M phase) at the given working temperature T and a second phase transformation temperature Af2 higher than the first phase transformation temperature Af1 and the third phase transformation temperature Af3. Further, yield stress (or yield point) of the second region 120 has a value lower than the yield stress of the first region 110 and the third region 130. Accordingly, the second region 120 is a region where plastic deformation occurs more easily than the first region 110 and the third region 130.

For example, in the case where the tube member 200 is made of a nickel-titanium alloy, also known as Nitinol, if the nickel-titanium alloy is subjected to cold forging, cold rolling, cold extrusion, or cold drawing and thus has the form of a tube, the tube has high strength because of work hardening so that it is not easily deformed by an external force and has high elasticity. The cold-worked tube has the crystal grains elongated in a given direction or the characteristics of microstructures such as grain refinement according to the worked methods. If the cold-worked tube is subjected to a heat treatment in next step, changes in the microstructures and the properties of the alloy are made.

For example, if the alloy is subjected to the heat treatment at a given temperature after cold-worked, the alloy has the characteristics of phase transformation according to heating and cooling. That is, the alloy has the characteristics of phase transformation so that it has the austenite phase at a temperature higher than its phase transformation temperature and the martensite phase at a temperature lower than its phase transformation temperature. A temperature at which the phase transformation occurs is in the range from $-100^\circ$ C. to $100^\circ$ C. according to the components of the nickel-titanium alloy or the heat treatment methods. With the heat treatment, further, the shape of the tube member is memorized and the microstructure thereof is changed, thereby applying the characteristics of hyperelasticity or shape memory effect to the alloy.

The second region 120, which has the martensite phase at a temperature lower than the second phase transformation temperature Af2, may be deformed by means of reversible movements of a twinning plane in the martensite phase. Accordingly, the second region 120 needs an extremely small force for deformation so that it is felt that it is gently deformed, and if stress is removed from the second region 120, the second region 120 stays in the deformed state like general metals so that it can be easily made to a desired form. In this case, strain occurring by the movements of the twinning plane is 7 to 8% of tensile strain, and after deformed, if the second region 120 is heated to a temperature higher than the second phase transformation temperature Af2, it transforms into the austenite phase and has the shape memory effect so that it recovers to its original shape before the deformation.

In the case of the alloy having the shape memory effect, the austenite phase has the characteristics of hyperelasticity and high stiffness, whereas the martensite phase has the mechanical characteristics so that it is easily deformed even at low stress.

As shown in FIG. 3(a), if the second phase transformation temperature Af2 of the second region 120 of the tube member 200 is set to a temperature higher than the working temperature T by means of the adjustment of heat treatment conditions, the second region 120 can have the martensite phase at the working temperature T.

If the tube member is used as a surgical instrument for the paranasal sinuses, the working temperature T is a room temperature at which the tube member is locally bent when surgery is carried out by a surgeon or a temperature of a human body directly contacted with the tube member, and that is, the working temperature T is in the range from 10 to $50^\circ$ C., desirably, in the range from 20 to $40^\circ$ C.

In the case where the tube member is used as the surgical instrument for the paranasal sinuses, accordingly, the second region 120 of the tube member 200 has the martensite phase at the working temperature T, and the second region 120 is freely bent according to the angles of the paranasal sinuses of a patient so that it is easily made to a bent shape as required. In specific, the working temperature T as the body temperature of the patient is lower than the second phase transformation temperature Af2 of the second region 120, and accordingly, the second region 120 having the martensite phase is freely bent.

As another example, if the tube member is used as a guide member for inserting a member such as an electric wire and the like located at a position where a worker's hand does not reach in various working sites, the working temperature T is set in the range of a temperature similar to a room temperature in his or her working environments.

In this case, even though all of the regions 110, 120, and 130 of the tube member 200 have the martensite phases at the working temperature T, a minimal degree of bending may occur. However, if all of the regions 110, 120, and 130 of the tube member 200 are freely deformed, even the first region 110 or the third region 130 is deformed so that it is hard to deform the second region 120 to a desired angle. Further, when the tube member 200 is inserted into the human body, the first region 110 or the third region 130 is unnecessarily deformed easily, thereby lowering a working efficiency such as the patient's treatment, and the like.

As shown in FIG. 3(b), accordingly, the first phase transformation temperature Af1 and the third phase transformation temperature Af3 of the first region 110 and the third region 130 excepting the second region 120 requiring free bending are set lower than the working temperature T, so that the first region 110 and the third region 130 have the austenite phases in which deformation does not occur easily at the working temperature T.

Accordingly, the respective regions 110, 120, and 130 of the tube member 200 have different characteristics according to their role, so that the first region 110 having the austenite phase at the working temperature T is utilized as a handle or a part connected to a handpiece, the second region 120 having the martensite phase is easily deformed and utilized as a portion at which the bending angle is adjusted, and the third region 130 having the austenite phase is utilized as a portion coupled or bonded to the cutting member S having a saw blade.

As a modified example, the second region 120 of the tube member 200 has the martensite phase, and both the first region 110 and the third region 130 or either the first region 110 or the third region 130 are (is) cold-worked at the working temperature. In this case, the cold-worked region has a minimal degree of stiffness because of work hardening.

Now, a method for manufacturing the tube member 200 having excellent local bending properties according to the present invention will be explained in detail below.

Figure 4:
FIGS. 4 to 6 are sectional views showing the steps of manufacturing the tube member having excellent local bending properties according to the present invention.
Figure 5:
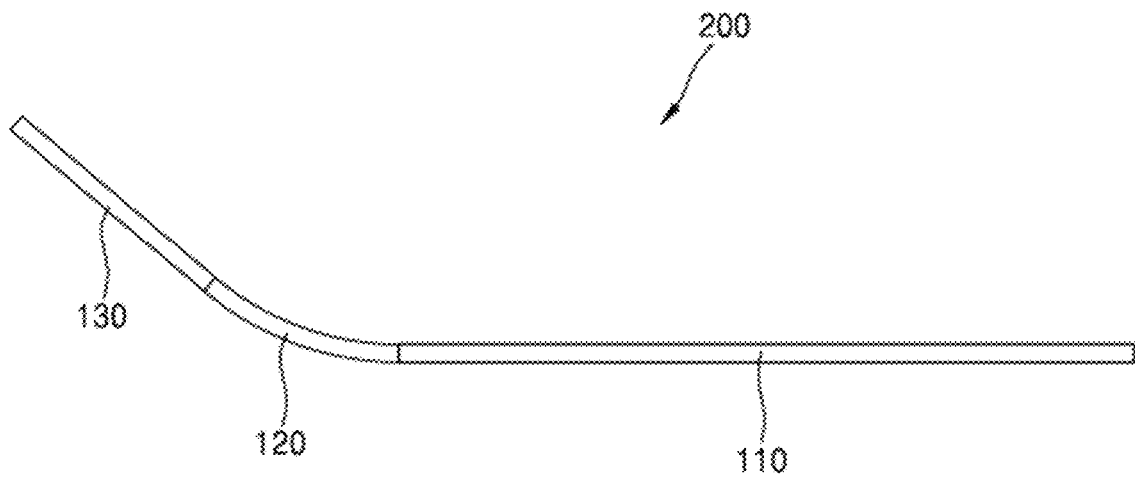
Figure 6:
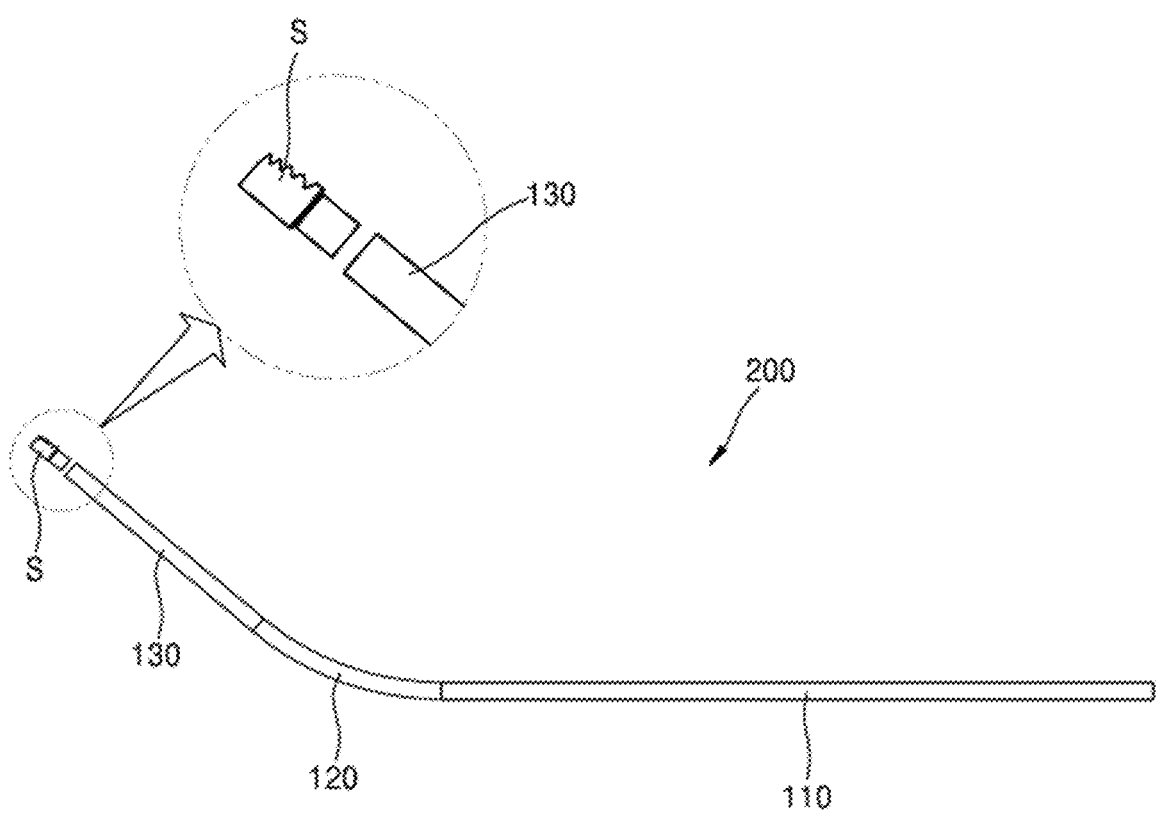
Figure 9:
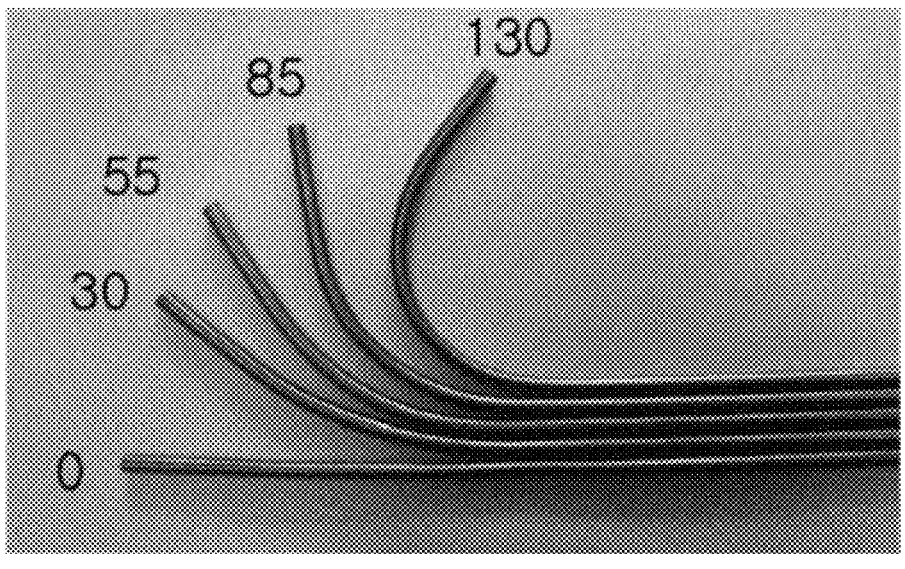

FIGS. 4 to 6 are sectional views showing the steps of manufacturing a tube member 200 having excellent local bending properties according to the present invention, and FIG. 9 is an image showing the real products of the tube members having excellent local bending properties according to the present invention.

First, as shown in FIG. 4, an alloy having shape memory effect, such as a Ni—Ti alloy, is cold-worked to the shape of a tube so that a straight line-shaped tube member 200, which is divided into a first region 110, a second region 120, and a third region 130, is prepared. The tube member 200 is subjected to cold working such as cold forging, cold rolling, cold extrusion, or cold drawing and has the shape of the generally straight line-shaped tube. In this case, because the tube member 200 is just cold-worked, it has substantially high stiffness like common alloys.

Next, as shown in FIG. 5, at least a portion of the second region 120 of the tube member 200 is bent to a given angle before the tube member 200 is subjected to a heat treatment. In this case, the bending angle of the second region 120 is set in consideration of the range of the bending angle as required by a user. For example, if the straight line-shaped tube member 200 is bent, the tube member 200 is bent within the range of about 100°, without any damage on the sectional area thereof. In specific, if the desired bending angle of the tube member 200 is in the range from 0 to 120°, the second region 120 is bent to the angle of about 40° before the tube member 200 is subjected to the heat treatment, and accordingly, the ranges of the bending angle needed can be all accepted.

Further, the first region 110 and the third region 130, which require given strength with which deformation does not occur easily so that the first region 110 serves as a support body and the third region 130 is coupled to a cutting member S, excepting the second region 120 requiring the free bending, are kept cold-worked, without any heat treatment or have the phase transformation temperatures lower than a working temperature T by means of the heat treatment so that they are kept in a hyperelastic state at the working temperature T.

For example, only the second region 120 of the tube member 200 is subjected to the heat treatment so that the first region 110 and the third region 130 are kept cold-worked and the second region 120 has a second phase transformation temperature Af2 higher than the working temperature T. For example, in the case of the Ni—Ti alloy, a temperature of the heat treatment is in the range from 400 to 450° C. The heat treatment for the second region 120 is performed by local heating using laser, and otherwise, only the second region 120 is accommodated in a heat treatment chamber and locally heated. However, the heat treatment methods may be freely performed only if the second region 120 is locally heated, without being limited thereto.

Accordingly, the second region 120 of the tube member 200 has the second phase transformation temperature Af2 higher than the working temperature T so that it has a martensite phase at the working temperature T. In this case, because the first region 110 and the third region 130 are just cold-worked, they have substantially high stiffness like common alloys.

Accordingly, the second region 120 of the tube member 200 is easily deformed even with a small force, and even when the small force is removed, the second region 120 is kept at the deformed state. Contrarily, the first region 110 and the third region 130 are not easily deformed even with the application of a given force, and when the force is removed, they quickly recover to their original shape because of their stiffness, so that in the state where the first region 110 or the third region 130 with high stiffness is grasped by the user or coupled to another grip part, the second region 120, which is easily deformed because of its martensite phase, is freely bent. The above-mentioned tube member manufacturing method is applicable in the case where the third region 130 is directly machined to make the cutting member S thereon, without inserting the cutting member S thereinto.

If the cutting member S is insertedly coupled to the third region 130, it is necessary to apply the heat treatment to the third region 130 so as to easily insert the cutting member S into the third region 130.

For example, all of the regions 110, 120, and 130 of the tube member 200 are subjected to a first heat treatment at a first temperature so that the tube member 200 having the second region 120 bent to the given angle after cold-worked has a first phase transformation temperature Af1 lower than the working temperature T. Next, only the second region 120 of the tube member 200 is subjected to a second heat treatment at a second temperature so that it has the second phase transformation temperature Af2 higher than the working temperature T, which allows the phase transformation temperature of the second region 120 to be set again. In this case, if the tube member 200 is made of the Ni—Ti alloy, a temperature for the first heat treatment is in the range from 500 to 550° C., and a temperature for the second heat treatment is in the range from 350 to 450° C. according to the compositions thereof.

Next, as shown in FIG. 6, only the third region 130 of the tube member 200 is locally cold to a temperature lower than the first phase transformation temperature Af1, and accordingly, the third region 130 has a martensite phase. After that, one end of the third region 130 easily deformable because of the martensite phase formed by colding is expanded to insert the cutting member S thereinto. In this case, the inserted portion of the cutting member S into the third region 130 has an outer diameter somewhat larger than an inner diameter of the third region 130 before expanded.

After that, if the third region 130 is raised in temperature to a temperature higher than the first phase transformation temperature Af1, one end expanded of the third region 130 is contracted again to allow the cutting member S to be forced-fitted thereto with a strong force. In this case, the temperature of the cold third region 130 is raised by means of separate heating, but in the case where the phase transformation temperature is set lower than the room temperature, the temperature of the cold third region 130 is raised as the cold third region 130 is left at the room temperature.

As a modified example, even in the case where the tube member 100 having the first region 110 and the second region 120 is manufactured, the same steps excepting the steps performed for the third region 130 are performed, and accordingly, an explanation of the method for manufacturing the tube member 100 will be avoided for the brevity of the description.

Hereinafter, manufacturing examples according to the present invention will be described to allow the present invention to be easily understood. The manufacturing examples as will be described below are just exemplary, and therefore, the present invention may not be limited to the manufacturing examples.

First Manufacturing Example

A straight line-shaped tube member made of a Ni—Ti alloy (50.2 at % Ni) and subjected to cold working was prepared. A portion of the tube member was bent to 30° and only the bent portion (the second region of the tube member) was subjected to a heat treatment above a temperature of 350° C. After the heat treatment, the bent portion was deformedly shaped and had a phase transformation temperature of 45° C., so that the bent portion had a martensite phase at a working temperature (room temperature or a user's body temperature).

Figure 7:
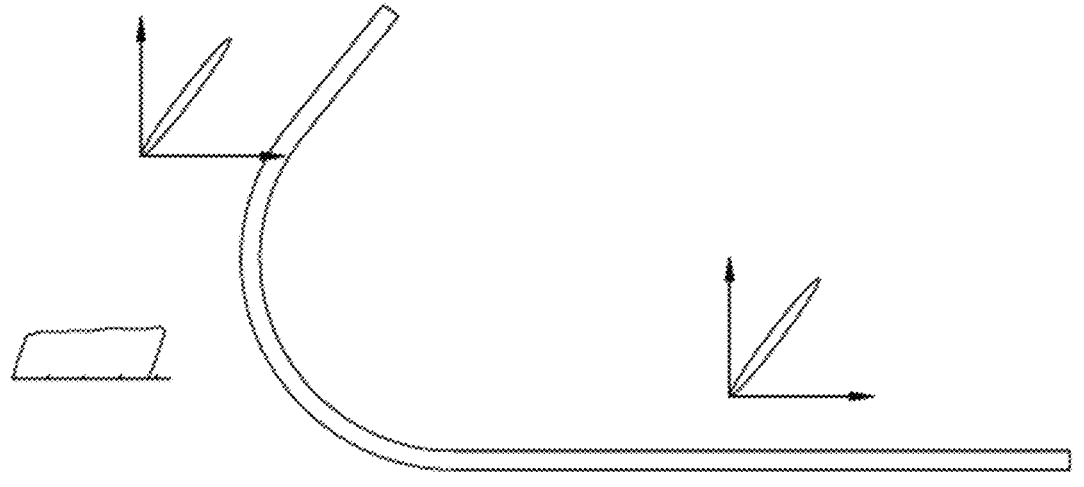
FIGS. 7 to 10 are sectional views showing the examples of the manufactured tube members having excellent local bending properties according to the present invention.

FIG. 7 shows the tube member manufactured by the first manufacturing example. If the bent portion is deformed, a gentle deformation behavior is made, and the remaining portion with no heat treatment is in the cold-worked state, thereby causing a very strong behavior. In FIG. 7, stress-strain graphs representing elasticity as the mechanical characteristics of the cold-worked alloy are shown together with the corresponding portions to the first region and the third region. Further, a stress-strain graph in which plastic deformation occurs even in low stress is shown together with the corresponding portion to the second region.

Second Manufacturing Example

A straight line-shaped tube member made of a Ni—Ti alloy (50.6 at % Ni) and subjected to cold working was prepared. A portion of the tube member was bent to 40° and the entire tube member was subjected to a heat treatment at a temperature of 500° C. for 5 minutes or more. After the heat treatment, the tube member had a phase transformation temperature of about 15° C. lower than a working temperature in the range of room temperature or a user's body temperature, so that the tube member had a hyperelastic behavior.

Figure 8:
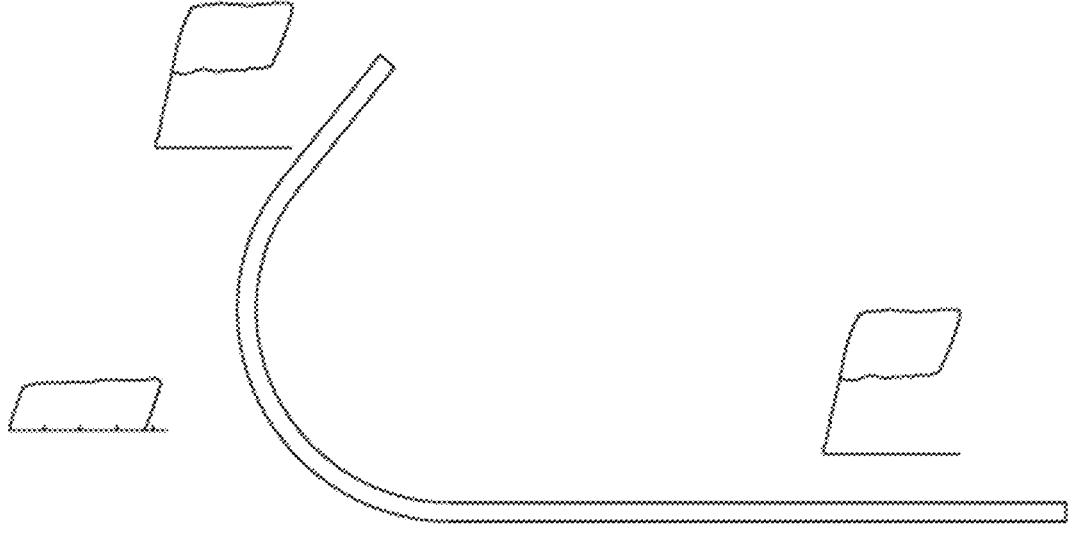

In this case, if only the bent portion was subjected to a heat treatment at a temperature of 450° C., the phase transformation temperature was raised, so that the bent portion with the additional heat treatment had a gentle deformation behavior, and the remaining portion had a hyperelastic behavior. If heating at the temperature of 450° C. was performed, $Ni_4T_{13}$ precipitates were produced so that Ni concentration of a substrate was lowered to cause the phase transformation temperature to rise. As a result, the tube member had the behavior characteristics as shown in FIG. 8. In FIG. 8, stress-strain graphs representing hyperelasticity are shown together with the corresponding portions to the first region and the third region. If the tube member is deformed, the bent portion is easily bent to various angles as shown in FIG. 9.

Figure 10:
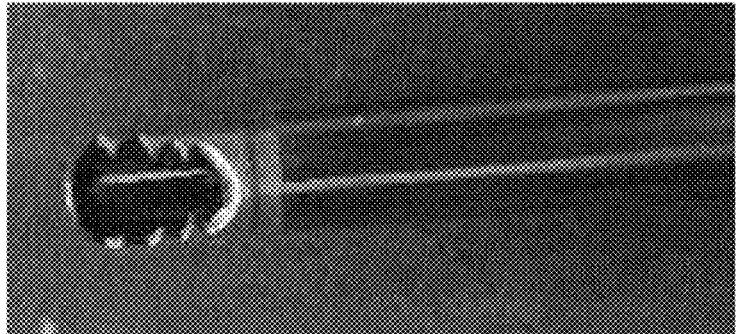

Next, the step of inserting a cutting member into the corresponding portion to the third region was performed. The inner diameter of the tube member was 3.6 mm, and accordingly, a stainless saw blade with a diameter of 3.7 mm larger than the inner diameter of the tube member was prepared. Only the corresponding portion to the third region was locally cold and thus had a temperature below a room temperature to expand an inlet of the end portion of the tube member. Next, the prepared cutting member was inserted into the expanded portion, and the corresponding portion to the third region was raised in temperature to the room temperature again. The inner diameter of the tube member was contracted at the room temperature to make the cutting member tightly fastened, so that the tube member was strongly coupled to the cutting member. FIG. 10 shows the tube member to which the cutting member is coupled.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above teachings. It is therefore intended that the scope of the invention be limited not by this detailed description, but rather by the claims appended hereto.

EXPLANATIONS OF REFERENCE NUMERALS

110: First region
120: Second region
130: Third region
100, 200: Tube member
S: Cutting member
T: Working temperature
Af1: First phase transformation temperature
Af2: Second phase transformation temperature
Af3: Third phase transformation temperature

INDUSTRIAL APPLICABILITY

The tube member according to the present invention is applicable to all kinds of working sites so that it can be freely bent and used by the user.

The invention claimed is:

1. A tube member used as a surgical instrument for a paranasal sinus, the tube member comprising:
   a first region and a third region, each having an austenite phase at a working temperature at which a surgery is performed; and
   a second region connecting the first region and the third region, the second region having a martensite phase and having a bent shape at a predetermined angle at the working temperature,
   wherein the tube member is made of a shape memory alloy and is configured to be inserted into the paranasal sinus,
   wherein the first region has a first phase transformation temperature lower than the working temperature,
   wherein the second region has a second phase transformation temperature higher than the working temperature,
   wherein the third region has a third phase transformation temperature lower than the working temperature,
   wherein the first phase transformation temperature, the second phase transformation temperature, and the third phase transformation temperature are temperatures at which a phase transformation from a low temperature martensite phase to a high temperature austenite phase occurs,
   wherein the second phase transformation temperature of the second region is higher than both the first phase transformation temperature of the first region and the third phase transformation temperature of the third region, wherein a yield stress of the second region is lower than a yield stress of the first region, and wherein the second region is configured to:

retain the bent shape in the martensite phase at the working temperature, and upon being heated to a temperature higher than the working temperature, undergo phase transformation to the austenite phase and recover a pre-bent shape, exhibiting a shape memory behavior.

2. The tube member according to claim 1, wherein the third phase transformation temperature is equal to the first phase transformation temperature.

3. The tube member according to claim 1, wherein one end of the third region, which is the other end of the tube member, is coupled to a cutting member.

4. The tube member according to claim 1, wherein the working temperature is in a range from 10 to 50° C.

5. The tube member according to claim 1, wherein the tube member includes a guide tube member configured to receive an electric wire inserted therein.

6. The tube member according to claim 1, made of any one of a nickel-titanium (Ni—Ti) alloy, a copper-zinc (Cu—Zn) alloy, a gold-cadmium (Au—Cd) alloy, and an indium-thallium (In—Ti) alloy.

7. The tube member according to claim 1, wherein the first region, the second region, and the third region are seamlessly integrated in the tube member.

8. A method for manufacturing a tube member used as a surgical instrument for a paranasal sinus, the method comprising:

cold-working a shape-memory alloy into a tubular shape to prepare a straight tube member having a first region, a second region, and a third region;

bending at least a portion of the second region of the tube member to a predetermined angle;

subjecting an entire tube member to a first heat treatment at a first heating temperature to transform the entire tube member into an austenite phase;

locally subjecting the second region of the tube member to a second heat treatment at a second heating temperature to transform the second region into a martensite phase;

locally cooling the third region of the tube member to a temperature lower than a first phase transformation temperature;

expanding one end of the cooled third region and coupling a cutting member thereto; and raising a temperature of the third region to a temperature higher than the first phase transformation temperature, wherein each of the first region, the second region, and the third region have a respective phase transformation temperature at which a phase transformation from a low temperature martensite phase to a high temperature austenite phase occurs, wherein the first heat treatment and the second heat treatment are performed to allow heat-treated regions to undergo phase transformations from the low temperature martensite phase to the high temperature austenite phase, wherein a second phase transformation temperature of the second region is higher than a working temperature at which the bending of the at least a portion of the second region is performed, and wherein the second region is configured to:

retain a bent shape in the martensite phase at the working temperature, and upon being heated to a temperature higher than the working temperature, undergo phase transformation to the austenite phase and recover a pre-bent shape, exhibiting a shape memory behavior.

9. The method according to claim 8, wherein the tube member is made of any one of a nickel-titanium (Ni—Ti) alloy, a copper-zinc (Cu—Zn) alloy, a gold-cadmium (Au—Cd) alloy, and an indium-thallium (In—Ti) alloy.

10. The method according to claim 8, wherein the first heating temperature is in a range from 500° C. to 550° C., and the second heating temperature is in a range from 350° C. to 450° C.

11. The method according to claim 8, wherein the cutting member has an outer diameter larger than an inner diameter of the one end of the third region prior to expansion, and after the cutting member is inserted into the expanded one end of the third region, the expanded one end of the third region contracts by raising the temperature of the third region to the temperature higher than the first phase transformation temperature, thereby force-fitting the cutting member into the contracted one end of the third region.

* * * * *